United States Patent [19]

Berggren

[11] Plant 4,452

[45] Aug. 21, 1979

[54] ROSE PLANT—GABRIELLA

[75] Inventor: Lars Berggren, Vällingby, Sweden

[73] Assignee: Jackson & Perkins Co., Medford, Oreg.

[21] Appl. No.: 859,793

[22] Filed: Dec. 12, 1977

[51] Int. Cl.[2] ..... A01H 5/00
[52] U.S. Cl. ..... Plt./28
[58] Field of Search ..... Plt./28

[56] References Cited

U.S. PATENT DOCUMENTS

P.P. 3,724 6/1975 Kordes ..... Plt./28

*Primary Examiner*—Robert E. Bagwill
*Assistant Examiner*—James R. Feyrer
*Attorney, Agent, or Firm*—Klarquist, Sparkman, Campbell, Leigh, Hall & Whinston

[57] ABSTRACT

This novel rose variety is a mutation of Mercedes and differs therefrom in its blossom colors which are a slightly darker shade of red than that of the parent variety.

5 Drawing Figures

DETAILED DESCRIPTION OF INVENTION

The present invention relates to a new and distinct variety of rose plant of the floribunda class, which was discovered by me as a cultivated sport of the floribunda rose Mercedes (U.S. Plant Pat. No. 3,724) on a plant grown in Vällingby, Sweden.

On the Mercedes rose bush, I discovered that flowers on one of the branches were distinctly different from a normal Mercedes, in both the tight bud and open flower. Propagation of the budding eyes of this one stem at Elmshorn, West Germany, and at Irvine, Calif., proved that this sport came through in successive propagations.

This new cultivar is substantially identical in all respect to its parent, except for the difference in bud and blossom color noted above. The attached drawing shows the stem, leaves, and blossom stages of the new cultivar.

As observed at Irvine, Calif., the new rose variety had a color in tight bud in accordance with Royal Horticultural Society Color Chart 45A. In the open flower, the color of the top of the petals was Wilson's Color Chart 721 and the reverse was Wilson's 721/3.

Being substantially identical to the parent variety except for the aforementioned distinctions, reference is made to U.S. Plant Pat. No. 3,724 for further description of this variety.

I claim:

1. A new and distinct variety of rose plant of the floribunda class, substantially as herein shown and described, characterized particularly as to novelty by the described difference in bud and bloom color set forth above on a plant otherwise identical to the variety Mercedes.

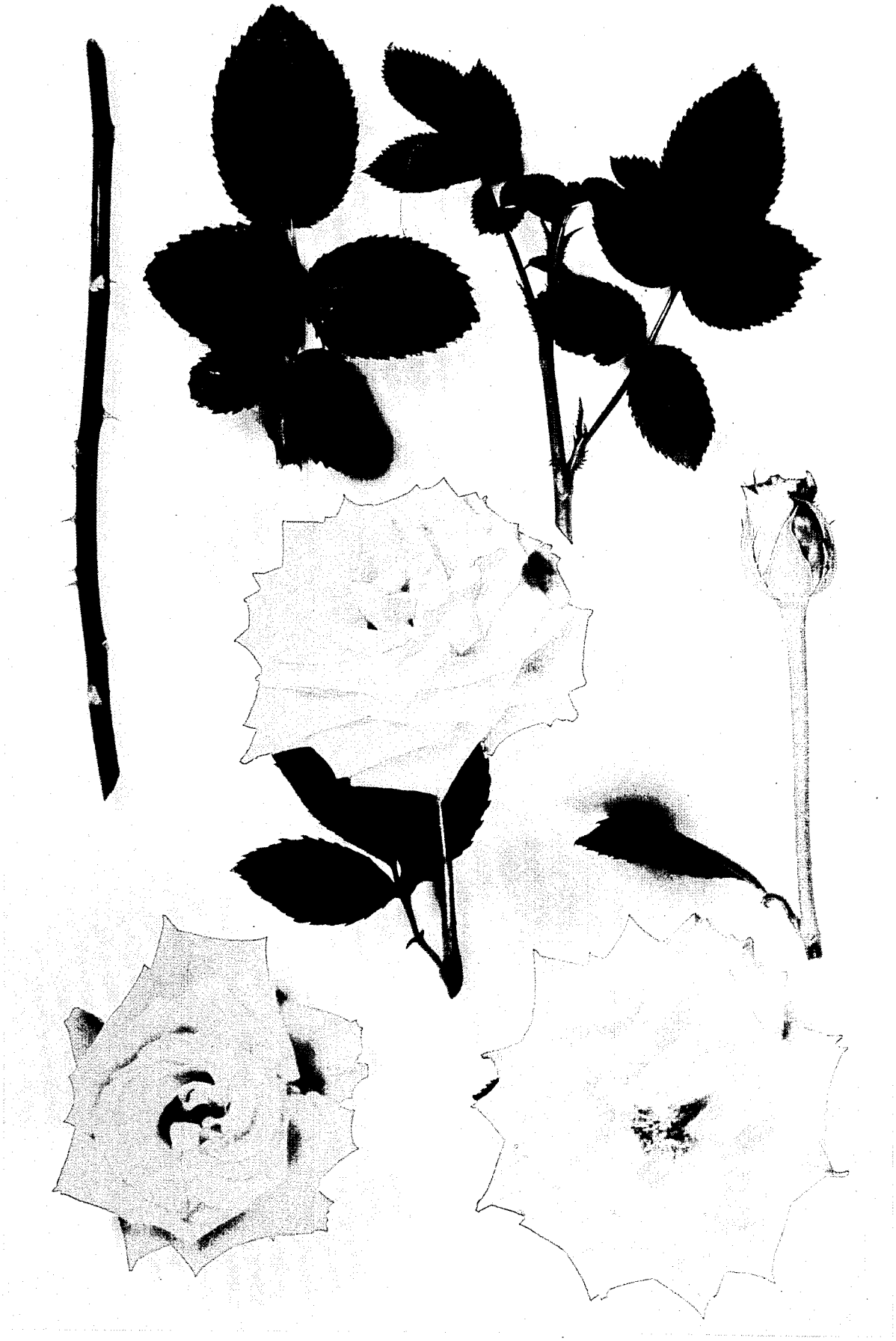

* * * * *